(12) United States Patent
Li et al.

(10) Patent No.: US 9,658,150 B2
(45) Date of Patent: May 23, 2017

(54) SYSTEM AND METHOD FOR SEMICONDUCTOR WAFER INSPECTION AND METROLOGY

(71) Applicant: KLA-TENCOR CORPORATION, Milpitas, CA (US)

(72) Inventors: Shifang Li, Pleasanton, CA (US); Youxian Wen, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/990,233

(22) Filed: Jan. 7, 2016

(65) Prior Publication Data
US 2016/0202177 A1 Jul. 14, 2016

Related U.S. Application Data

(60) Provisional application No. 62/102,312, filed on Jan. 12, 2015.

(51) Int. Cl.
*G01N 21/21* (2006.01)
*G01B 11/02* (2006.01)
(Continued)

(52) U.S. Cl.
CPC ............. *G01N 21/21* (2013.01); *G01B 11/02* (2013.01); *G01B 11/06* (2013.01); *G01B 11/30* (2013.01); *G01B 11/303* (2013.01); *G01N 21/9501* (2013.01); *G03F 7/70608* (2013.01); *G03F 7/70625* (2013.01); *G01N 2021/399* (2013.01);
(Continued)

(58) Field of Classification Search
CPC ............. G03F 7/70608; G03F 7/70616; G03F 7/70625; G03F 7/7065; G01B 11/02; G01B 11/06; G01B 11/0616; G01B 11/0641; G01B 11/30; G01B 11/303; G01B 11/306; G01N 2021/399; G01N 2021/8845; G01N 2021/8848; G01N 21/21; G01N 21/211; G01N 21/9501
See application file for complete search history.

(56) References Cited

U.S. PATENT DOCUMENTS 5,798,829 A * 8/1998 Vaez-Iravani ...... G01N 21/9501
356/237.1
7,271,921 B2 9/2007 Shortt
(Continued)

FOREIGN PATENT DOCUMENTS

WO 2014072109 A1 5/2014

OTHER PUBLICATIONS

ISA/KR, International Search Report for PCT/US2016/013199 Oct. 6, 2016.

*Primary Examiner* — Gordon J Stock, Jr.
(74) *Attorney, Agent, or Firm* — Hodgson Russ LLP

(57) ABSTRACT

A system determines a value, such as a thickness, surface roughness, material concentration, and/or critical dimension, of a layer on a wafer based on normalized signals and reflected total intensities. A light source directs a beam at a surface of the wafer. A sensor receives the reflected beam and provides at least a pair of polarization channels. The signals from the polarization channels are received by a controller, which normalizes a difference between a pair of the signals to generate the normalized result. The value of the wafer is determined through analyzing the signal with a modeling of the system.

20 Claims, 8 Drawing Sheets

(51) Int. Cl.
  *G03F 7/20* (2006.01)
  *G01B 11/30* (2006.01)
  *G01N 21/95* (2006.01)
  *G01B 11/06* (2006.01)
  *G01N 21/39* (2006.01)
  *G01N 21/88* (2006.01)

(52) U.S. Cl.
  CPC ............... *G01N 2021/8845* (2013.01); *G01N 2021/8848* (2013.01)

(56) References Cited

U.S. PATENT DOCUMENTS

| | | | |
|---|---|---|---|
| 2001/0013935 A1 | 8/2001 | Watanabe et al. | |
| 2002/0015146 A1* | 2/2002 | Meeks | G01B 11/065 356/73 |
| 2002/0105646 A1 | 8/2002 | Zhao et al. | |
| 2005/0094143 A1 | 5/2005 | Kubo et al. | |
| 2007/0165504 A1* | 7/2007 | Jann | G01B 11/306 369/53.15 |
| 2008/0198380 A1 | 8/2008 | Straaijer et al. | |
| 2008/0212096 A1 | 9/2008 | Kumar | |
| 2011/0246400 A1* | 10/2011 | Li | G01B 11/24 706/12 |
| 2013/0194572 A1* | 8/2013 | Goto | G01J 4/00 356/364 |
| 2014/0268149 A1* | 9/2014 | Zavislan | G01N 21/23 356/365 |
| 2015/0300809 A1 | 10/2015 | Kononchuk et al. | |

* cited by examiner

SYSTEM AND METHOD FOR SEMICONDUCTOR WAFER INSPECTION AND METROLOGY

CROSS-REFERENCE TO RELATED APPLICATIONS

This application claims priority to the provisional patent application filed Jan. 12, 2015 and assigned U.S. App. No. 62/102,312, the disclosure of which is hereby incorporated by reference.

FIELD OF THE DISCLOSURE

This disclosure relates to wafer inspection and metrology.

BACKGROUND OF THE DISCLOSURE

Semiconductor manufacturers print die as close to the wafer edge as possible to maximize the number of devices per wafer. However, die near the wafer edge typically show the lowest yield. To address edge-yield issues, semiconductor manufacturers need to control where the edge of each film lands, such as on the planar front surface of the wafer or past the planar surface into the sloped bevel. Semiconductor manufacturers also need to match the perimeter of each film to those of films deposited before and after it during device processing.

Current inspection and metrology tools are used for process control, such as for inspecting epitaxial wafers, inspecting and measuring photoresist edge bead removal (EBR), or inspecting z-cut height of a film at a wafer edge. These current inspection and metrology tools detect a signal and generate a phase image of a sample. However, per hardware construction and alignment procedures, there is no clear physical mean for these signals. It can be problematic to interpret the signal or link it to sample parameters, which has limited further development. Furthermore, since the collection efficiency of optics can vary from wafer to wafer at a wafer edge, from a metrology requirement point of view only one quantity can be deduced from the raw signals, which limits the amount of information that can be extracted from the signals.

Therefore, what is needed is a new system and method for wafer inspection and metrology.

BRIEF SUMMARY OF THE DISCLOSURE

In a first embodiment, a system is provided. The system includes a stage configured to hold a wafer; a light source configured to direct a beam at a surface of the wafer on the stage; a sensor configured to receive the beam reflected off the surface and provide at least two polarization channels; and a controller in electronic communication with the sensor. Each of the polarization channels provides a signal. The controller is configured to: receive the signal from each of the polarization channels; normalize a difference between a pair of the signals to generate a normalized result; and determine a value of a layer on the wafer based on the normalized result and a total intensity of the pair of the signals. The value is one of a thickness, a surface roughness, a material concentration, or a critical dimension. Each of the polarization channels can be generated by a polarizing beam splitter. The sensor can be a polarization sensitive detector.

In an instance, the sensor is configured to provide six of the polarization channels. The sensor in this instance includes: a first beam splitter; a second beam splitter configured to receive light from the first beam splitter; a first polarizing beam splitter configured to receive light from the first beam splitter; a second polarizing beam splitter configured to receive light from the second beam splitter; and a third polarizing beam splitter configured to receive light from the second beam splitter. The first polarizing beam splitter is configured to generate two of the six polarization channels. The second polarizing beam splitter is configured to generate two of the six polarization channels. The third polarizing beam splitter is configured to generate two of the six polarization channels. The first beam splitter can be a 30/70 beam splitter. The second beam splitter can be a 50/50 beam splitter. The second polarizing beam splitter can be at 45° and the third polarizing beam splitter can be at 0° with respect to an incident plane. A quarter waveplate can be disposed between the first beam splitter and the first polarizing beam splitter. The controller can be further configured to normalize pairs of the signals to generate three of the normalized results and determine the value based on the three normalized results.

The controller can be configured to normalize the difference between the pair of the signals using the formula $V=(Pq-Sq)/(Pq+Sq)$, wherein $Pq$ and $Sq$ are the pair of the signals, $V$ is the normalized result, and $Sp=Pq+Sq$ is the total intensity.

The sensor can be configured to provide four or fewer polarization channels of the beam reflected off the surface.

The light source can be configured to direct the beam at a plurality of wavelengths. The light source can be a tunable laser or a wavelength multiplex of a plurality of lasers working at different wavelengths.

The controller can be configured to determine the value of the layer by fitting the pair of the signals or the normalized result with a nonlinear least square optimization algorithm.

In a second embodiment, a method is provided. A method includes directing a beam from a light source at a surface of a wafer; receiving the beam reflected off the surface with a sensor; splitting the beam in the sensor into a plurality of polarization channels using at least one polarizing beam splitter; generating a signal from each of the polarization channels; normalizing a difference between a pair of the signals to generate a normalized result; and determining a value of a layer on the wafer based on the normalized results and a total intensity of the pair of the signals. The value is one of a thickness, a surface roughness, a material concentration, or a critical dimension.

The normalizing can use the formula $V=(Pq-Sq)/(Pq+Sq)$, wherein $Pq$ and $Sq$ are the pair of the signals, $V$ is the normalized result, and $Sp=Pq+Sq$ is the total intensity.

The splitting can further comprise splitting the beam into six of the polarization channels using three of the polarizing beam splitters. The normalizing can further comprise generating three of the normalized results.

The method can further comprise using a model to analyze the measured signals for determining the value of a layer on the wafer.

The beam can be at a plurality of wavelengths. The plurality of wavelengths can be generated by a tunable laser or by a wavelength multiplex of a plurality of lasers working at different wavelengths.

The determining can include fitting the pair of the signals or the normalized result with a nonlinear least square optimization algorithm.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure.

Embodiments of the systems and methods disclosed herein enable quantitative monitoring of sample parameters and provide improved inspection capabilities. The system generates more reliable and measurable quantities per point on the wafer per wavelength. This increases possible applications and improves results. Extracting sample parameters from an inspection tool can aid in detection of process parameter drift, which will enable semiconductor manufacturers to take preventive or corrective action.

Figure 1:
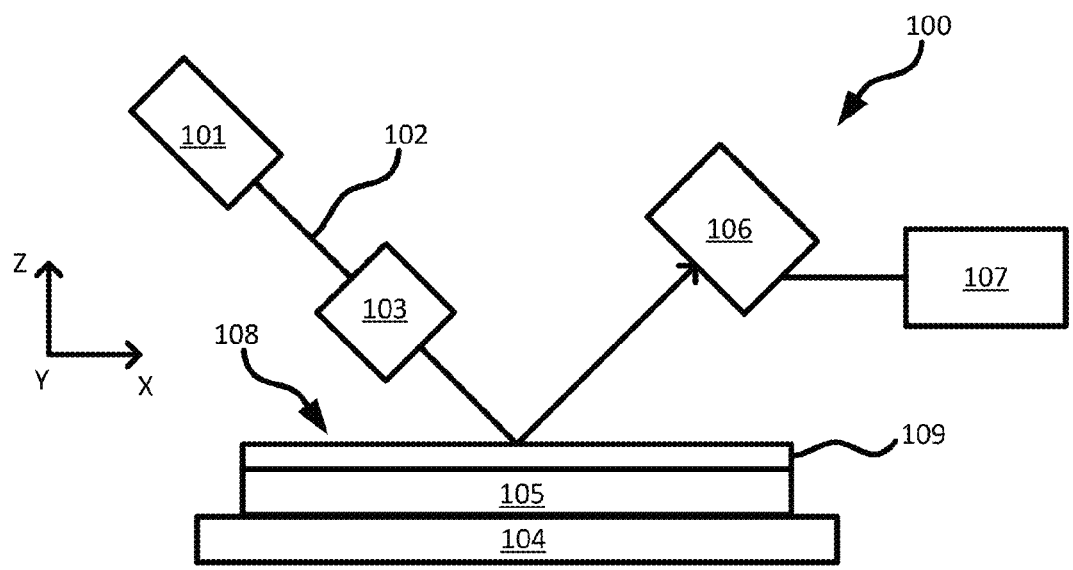
FIG. 1 is a schematic of an embodiment of a system in accordance with the present disclosure.

FIG. 1 is a schematic of an embodiment of a system 100. A light source 101 generates a beam 102 that is directed at a surface 108 of a wafer 105 on a stage 104. The beam 102 passes a polarization controller and focus mechanism 103 before emerging to the surface 108 of the wafer 105. The light source 101 may be a laser, such as a blue wavelength semiconductor laser in one embodiment. In another embodiment, the light source 101 may be a plurality of semiconductor lasers at different wavelengths combined with a wavelength multiplex technique to form a single beam 102. In yet another embodiment, the light source 101 may be a wavelength tunable semiconductor laser having a wavelength that is set based on a recipe parameter for a particular application. The beam 102 output is typically polarized with power in the range of a few to hundreds of mW. The light source 101 can be temperature controlled to improve its stability.

The stage 104 may be configured to scan the wafer 105 relative to the beam 102. This scanning by the stage 104 may be, for example, in the x-y plane. The light source 101 also may be configured to scan the beam 102 across the surface 108. The light source 101 can scan the beam 102 separately from or in conjunction with scanning the stage 104. The stage 104 may provide electrostatic, mechanical, or vacuum clamping of the wafer 105.

The wafer 105 may be, for example, a semiconductor wafer. The semiconductor wafer may be a 150 mm, 200 mm, 300 mm, or 450 mm diameter silicon wafer. The wafer 105 also can be other types of wafers, such as a wafer used to manufacture light-emitting diodes (LEDs) or solar cells.

The wafer 105 includes a layer 109. This layer 109 can be, for example, a layer that is epitaxially grown or deposited. In an instance, the layer 109 is a $Si_{1-x}Ge_x$ epitaxial layer protected by a top silicon cap layer. The layer 109 can be other types of layers besides a $Si_{1-x}Ge_x$ epitaxial layer.

The beam 102 may be directed through a polarization controller and focus mechanism 103 before reflecting off the surface 108 of the wafer 105. In an example, the polarization controller and focus mechanism 103 is a polarizer set at 45° from an incident plane. In another embodiment, the polarization controller and focus mechanism 103 includes a quarter waveplate following a polarizer with their optical axis offset by approximately 45°. The polarization controller and focus mechanism 103 may also include focus optics that control the beam spot size projected on the wafer 105.

The sensor 106 receives the beam 102 reflected off the surface 108 of the wafer 105 and provides at least a pair of polarization channels. Each pair of polarization channels has two photo-diode (PD) detectors that receive the pair of polarization states of the pair, respectively. Each pair of the PD detectors provides two intensity signals corresponding to two orthogonal polarization states. In an example, the sensor 106 is a polarization sensitive detector. The sensor 106 may have two, four, six, or more polarization channels that can be formed by one, two, three, or more paired polarization detectors. The sensor 106 can include a focus mechanism to collimate the light emerging from the surface 108. The focus mechanism can improve the polarization control accuracy of the sensor 106 and light collection efficiency.

The sensor 106 is in electronic communication with a controller 107. The controller 107 can include a processor, an electronic storage device in electronic communication with the processor, and a communication port in electronic communication with the processor. The processor can receive signals from the sensor, such as through an electronic connection. In an example, the controller 107 is configured to receive the signal for each of the polarization channels. The controller 107 then normalizes a difference between a pair of the signals to generate a normalized result. Based on the normalized result, the controller 107 determines a value of a layer on the wafer 105, such as the layer 109. The value may be, for example, a thickness, a surface roughness, a material concentration (e.g., Ge percentage, x, of a $Si_{1-x}Ge_x$ layer), and/or a critical dimension.

While a 45° orientation is illustrated in FIG. 1 for the polarization controller and focus mechanism 103, the polarization direction and polarizer orientation may be rotated to match the polarizer direction to optimize the system performance or control total intensity of the beam 102 emerging to the surface 108. The orientation of the polarizer in the polarization controller and focus mechanism 103 can be an angle larger or smaller than 45° to maximize the interference signal between reflected s- and p-polarization states. However, the polarization direction and polarizer orientation are not typically set at 0° or 90° with respect to an incident plane where there is no interference for an isotropic surface 108. In an instance, the polarization controller and focus mechanism 103 includes a quarter waveplate following the polarizer. The optical axis of the waveplate and polarizer is set at 45° to form circular polarized light emerging to the surface 108. A quarter waveplate with the polarization controller and focus mechanism 103 is optional and is not included in other instances.

Figure 2:
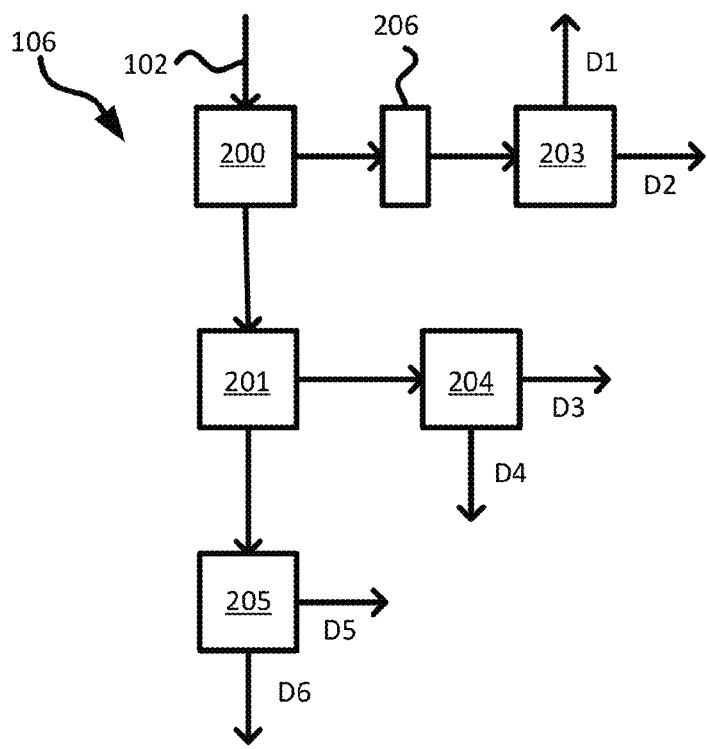
FIG. 2 is a schematic of an embodiment of the sensor of FIG. 1 in accordance with the present disclosure.

FIG. 2 is a schematic of an embodiment of the sensor 106 that has six polarization channels. The sensor 106 has a first beam splitter 200 and a second beam splitter 201 configured to receive light from the first beam splitter 200. A first polarizing beam splitter 203 is configured to receive light from the first beam splitter 200 and generate two of the six polarization channels (D1, D2). A second polarizing beam splitter 204 is configured to receive light from the second beam splitter 201 and generate two of the six polarization channels (D3, D4). A third polarizing beam splitter 205 is configured to receive light from the second beam splitter 201 and generate two of the six polarization channels (D5, D6). While the sensor 106 is illustrated in FIG. 2 as having six polarization channels, the sensor 106 can include other numbers of polarization channels.

Each pair of the three polarization channels in FIG. 2 can measure one or more different optical properties due to the configurations of the beam splitters and polarizing beam splitters. Thus, each pair of polarization channels can have unique properties. In an example, the first beam splitter 200 is a 30/70 beam splitter, the second beam splitter 201 is a 50/50 beam splitter, the second polarizing beam splitter 204 is at 45°, and the third polarizing beam splitter 205 is at 0° with respect to an incident plane, respectively. The sensor 106 includes a quarter waveplate 206 between the first beam splitter 200 and the first polarizing beam splitter 203. The optical axis of the quarter waveplate 206 and the first polarizing beam splitter 203 may be different by approximately 45°.

Figure 3:
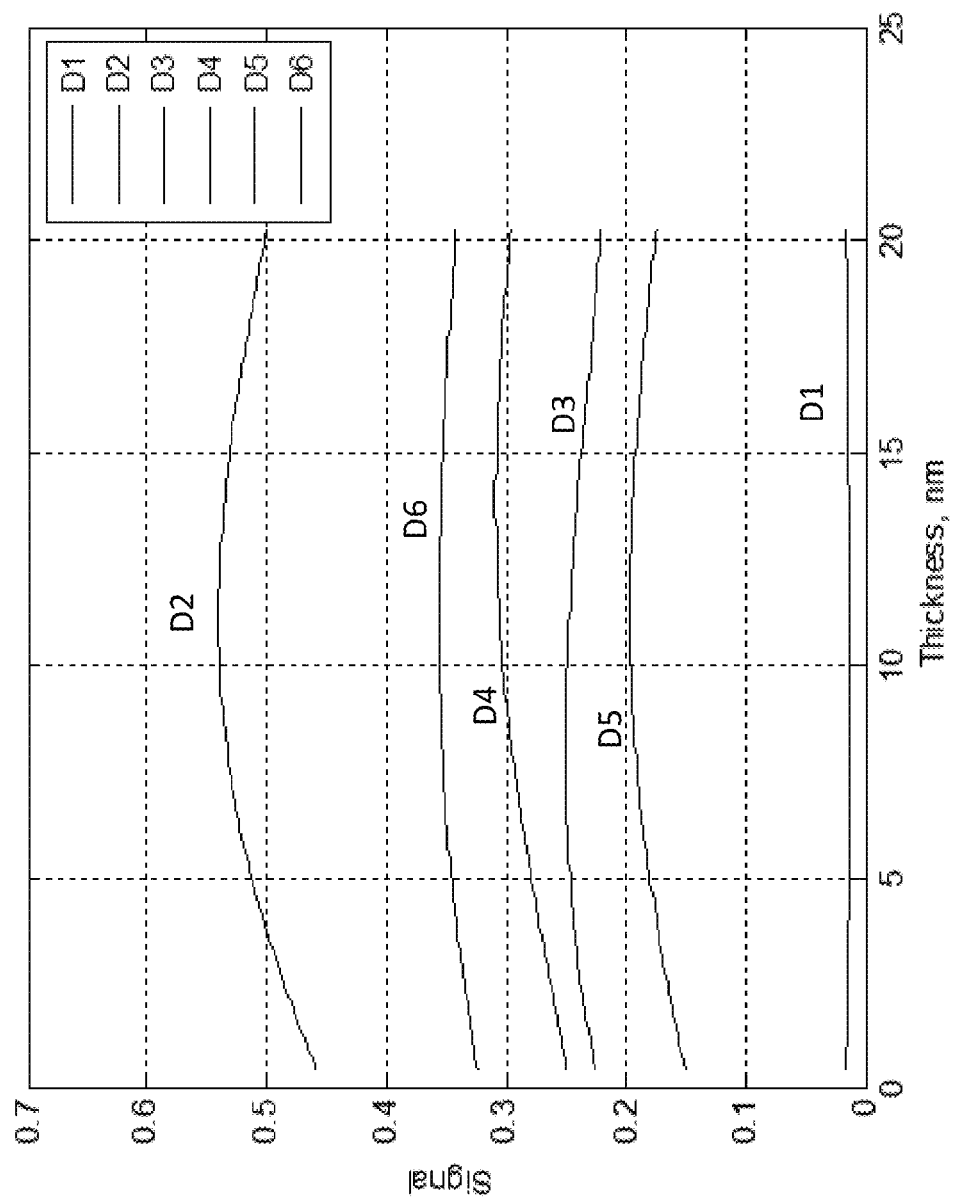
FIG. 3 is a graph comparing signal to thickness using the sensor of FIG. 2.

FIG. 3 is a graph comparing signal to thickness using the sensor 106 of FIG. 2. The six signals D1-D6 from each polarization channel are plotted. Signals from a pair of polarization channels, such as D1 and D2, can be used to determine a value of a wafer. These two signals can be referred to as Pq and Sq. Pq and Sq may be further analyzed to produce a phase image of the wafer edge. A normalized result from a pair of polarization channels also can provide improved accuracy or precision when determining the value, such as thickness, for a wafer.

In an example, signals from the pair of polarization channels are normalized using Equation 1.

$$V=(Pq-Sq)/(Pq+Sq) \quad \text{(Eq. 1)}$$

Pq−Sq can be referred to as Ph and Pq+Sq can be referred to as Sp. Pq and Sq are the pair of the signals, V is the normalized result, and Sp is the total intensity of the pair. V also can be referred to as visibility. In an instance, Pq and Sq are photonic signals that are real numbers.

Figure 4:
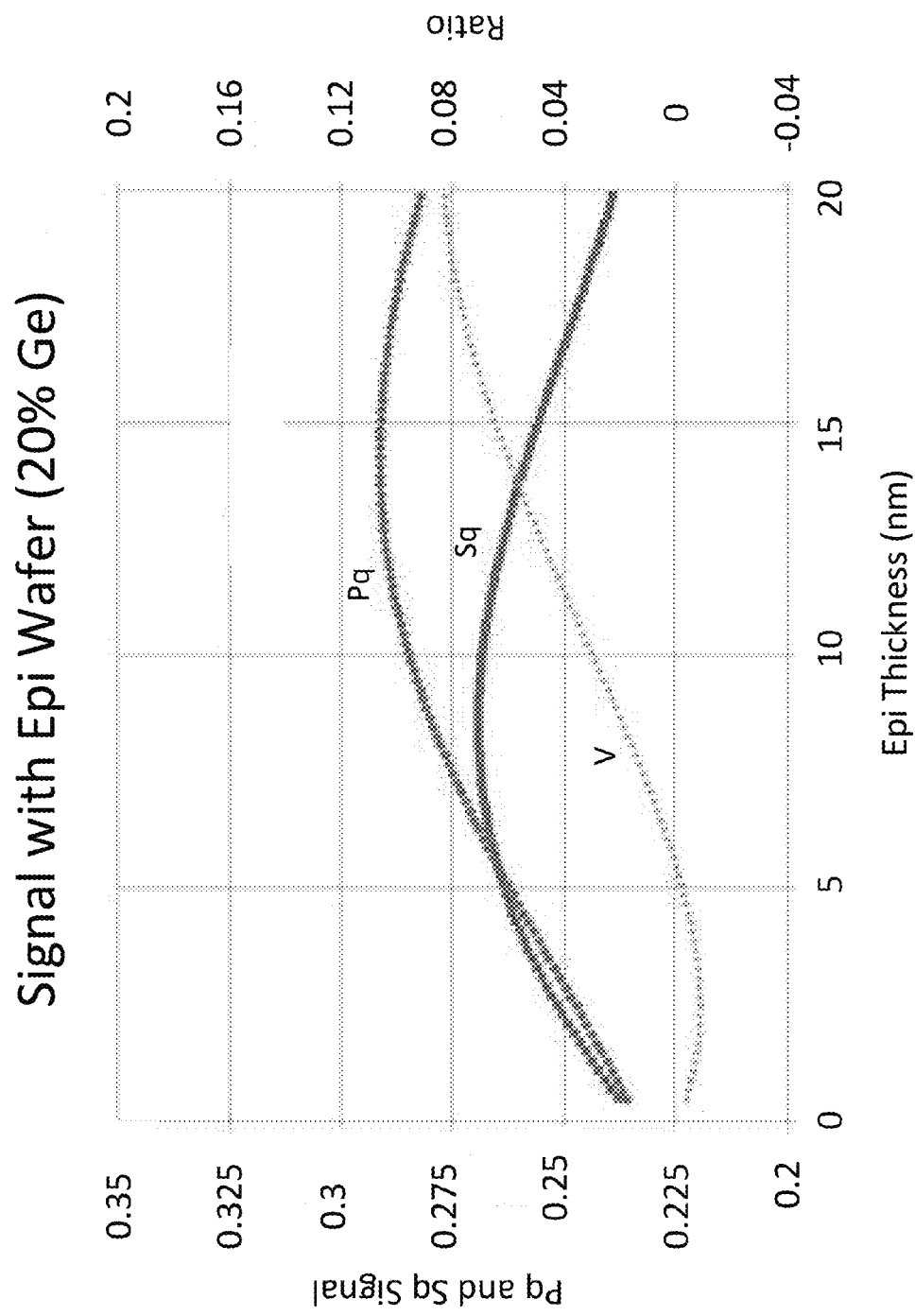
FIGS. 4-6 are graphs comparing signal to epitaxial layer thickness for $Si_{1-x}Ge_x$ epitaxial layers with different amounts of germanium.
Figure 5:
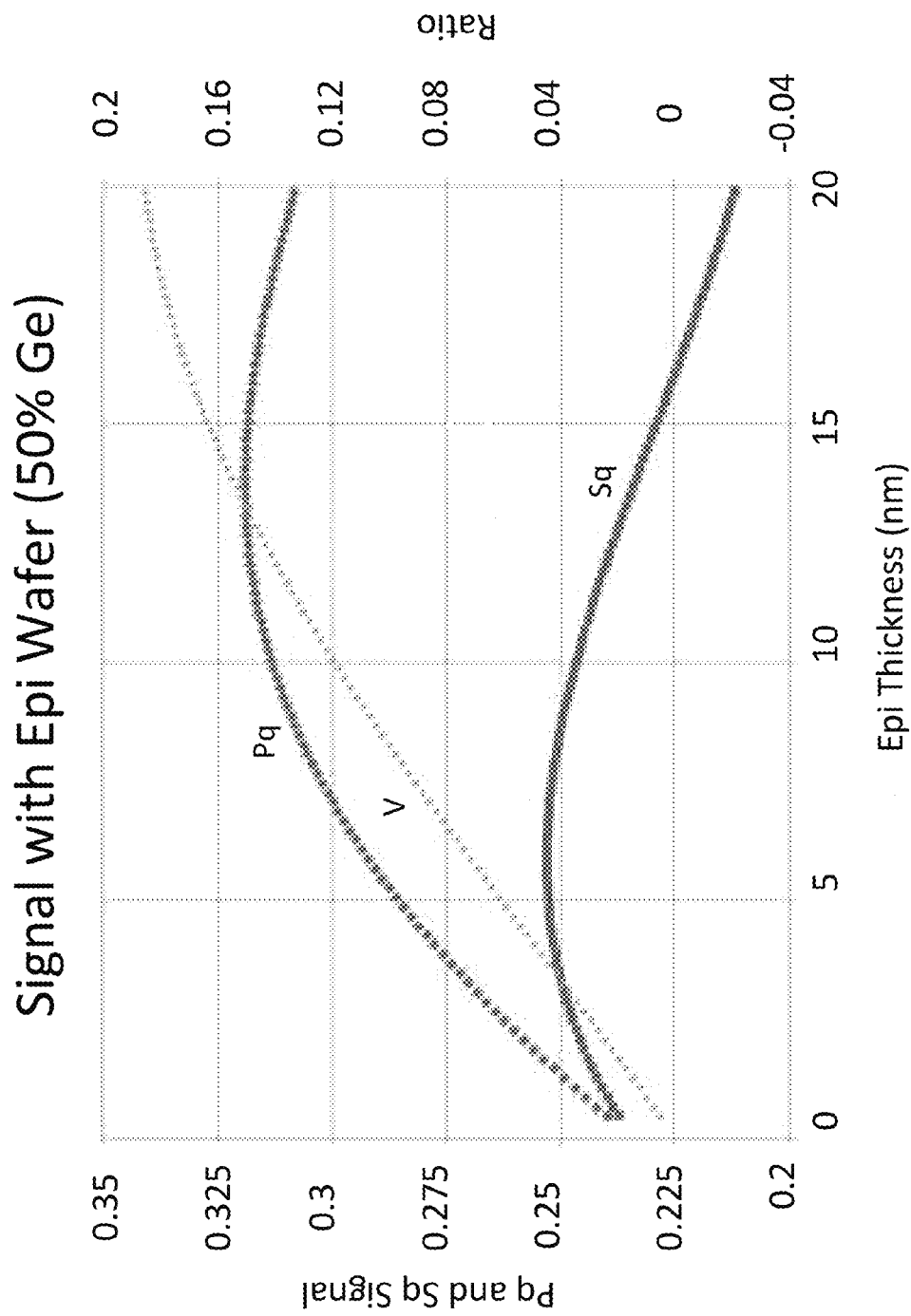
Figure 6:
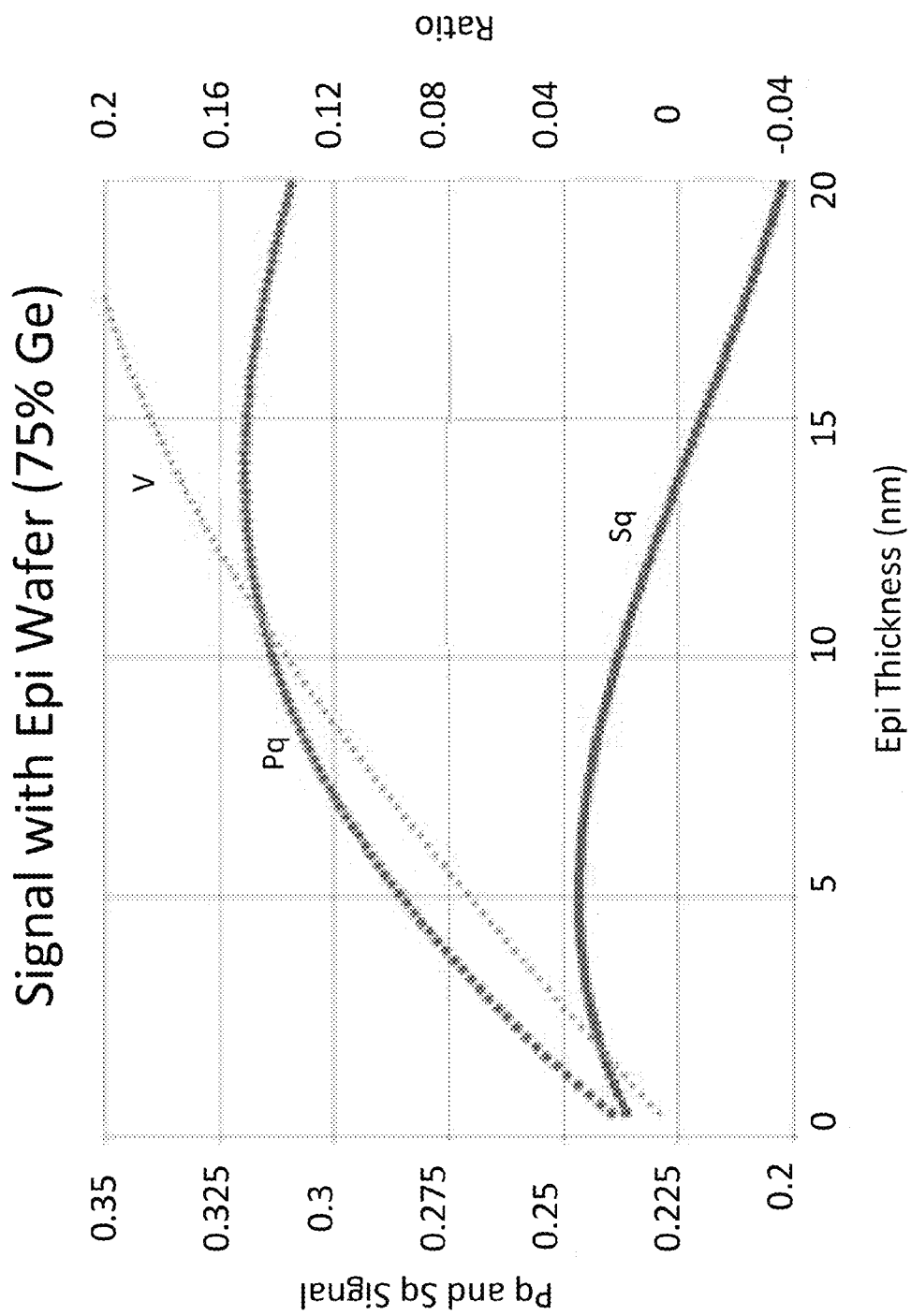

FIGS. 4-6 are graphs comparing signal to epitaxial layer thickness for $Si_{1-x}Ge_n$ epitaxial layers with different amounts of germanium (x). Each of FIGS. 4-6 plots Pq, Sq, and the resulting V calculated using Equation 1. V responds to epitaxial layer thickness and germanium concentration. As seen in FIGS. 5 and 6, V has a higher sensitivity to epitaxial layer thickness for higher germanium concentrations. V also reverses its sign at thin epitaxial layer thicknesses in samples with lower germanium concentrations, such as in FIG. 4.

The germanium concentration potentially affects V due to its optical properties. Germanium and silicon have different refractive indices and light absorption characteristics. Therefore, as the concentration of germanium in a $Si_{1-x}Ge_x$ epitaxial layer changes, the light reflected from the surface of the wafer changes. Other mechanisms regarding the effect of germanium concentration on V are possible. The signal variation with concentration of germanium provides the possibility of measuring Ge concentration through analyzing the measured signal V and Sp in additional to determining the thickness of a $Si_{1-x}Ge_x$ epitaxial layer.

Use of additional qualified numbers per point from the apparatus can improve determination accuracy of the value of the layer on the wafer. This can involve more wavelengths, such as using multiple lasers and pre-combining the incident beam paths directed toward the wafer using a wavelength multiplex technique. This may be separate wavelengths in the detector, time-multiplex that can modulate a laser and synchronize detection of the signal from each laser, or use a wavelength de-multiplex technique to send each wavelength to one of multiple sets of the sensor 106 seen in FIG. 1. More measurable signals per point per wavelength can be used to improve determination precision of the value of the layer on the wafer.

Figure 7:
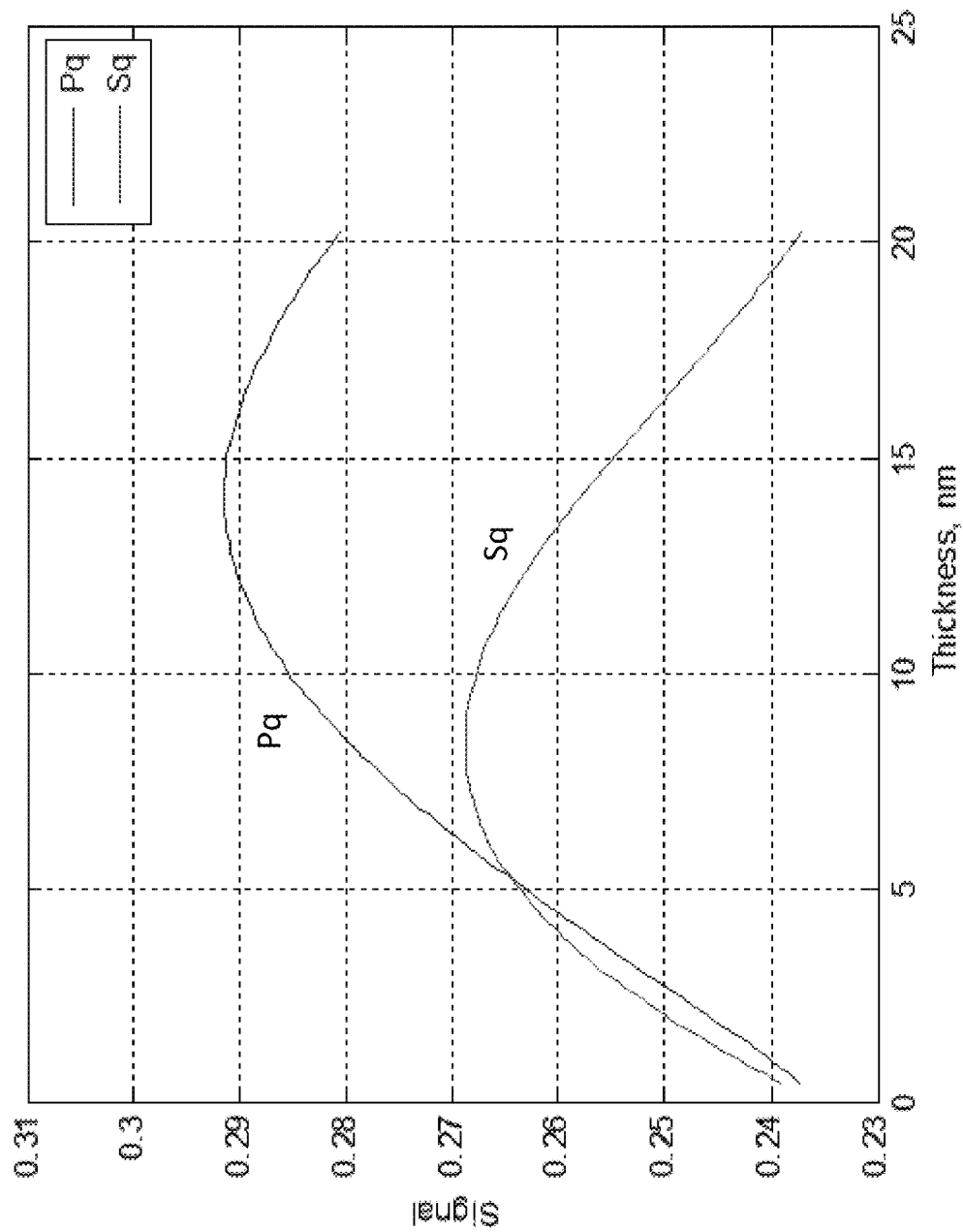
FIG. 7 is a graph comparing signal to thickness for Pq and Sq.
Figure 8:
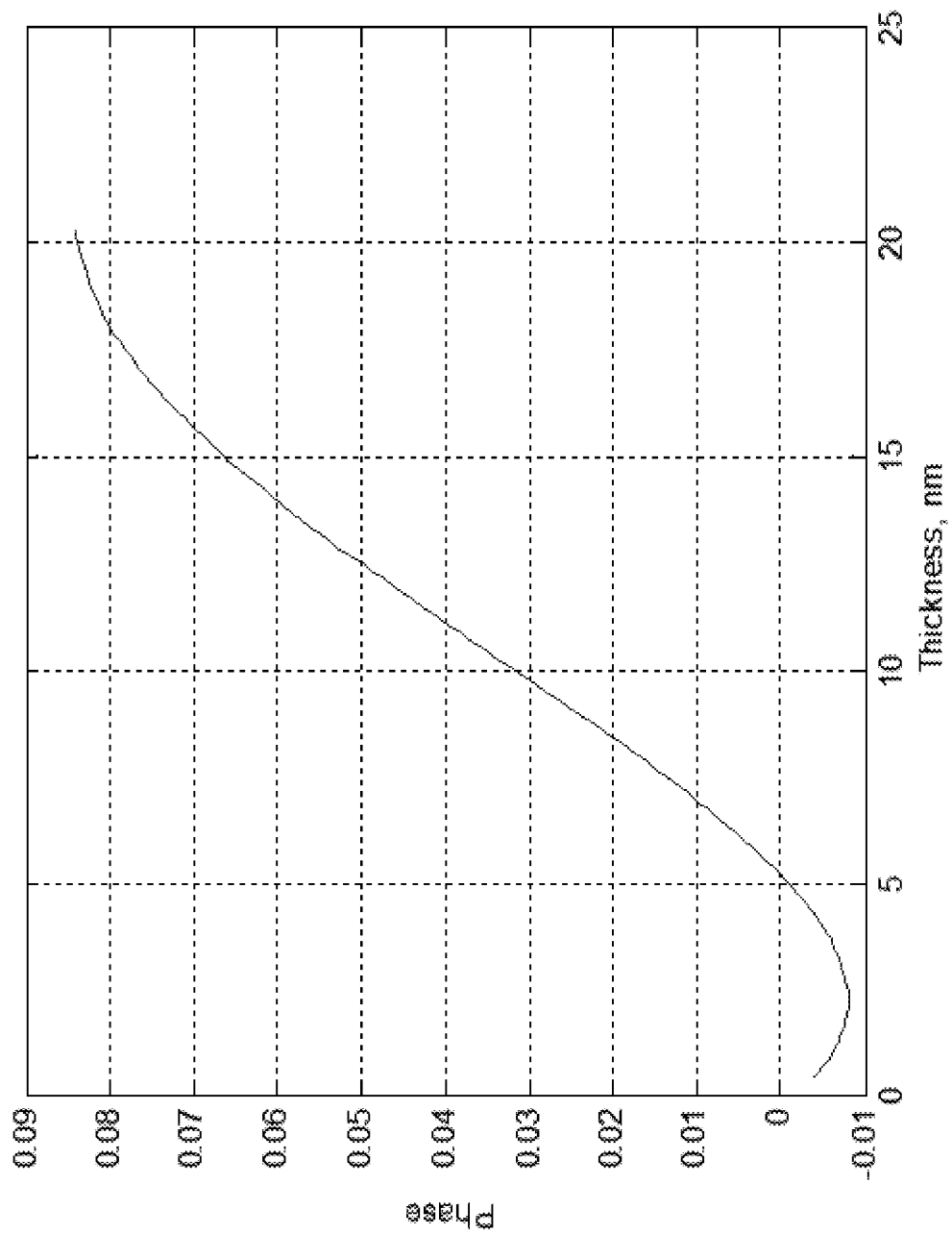
FIG. 8 is a graph comparing phase to thickness for the Pq and Sq of FIG. 7.

FIG. 7 is a graph comparing signal to thickness for Pq and Sq. FIG. 8 is a graph comparing phase to thickness for the Pq and Sq of FIG. 7. Pq and Sq may correspond to, for example, D1 and D2, D3 and D4, or D5, and D6, though only D1 and D2 are illustrated in FIGS. 7 and 8. The six signals from the sensor 106 are shown in FIG. 3 for the same wafer as in FIG. 7.

Figure 9:
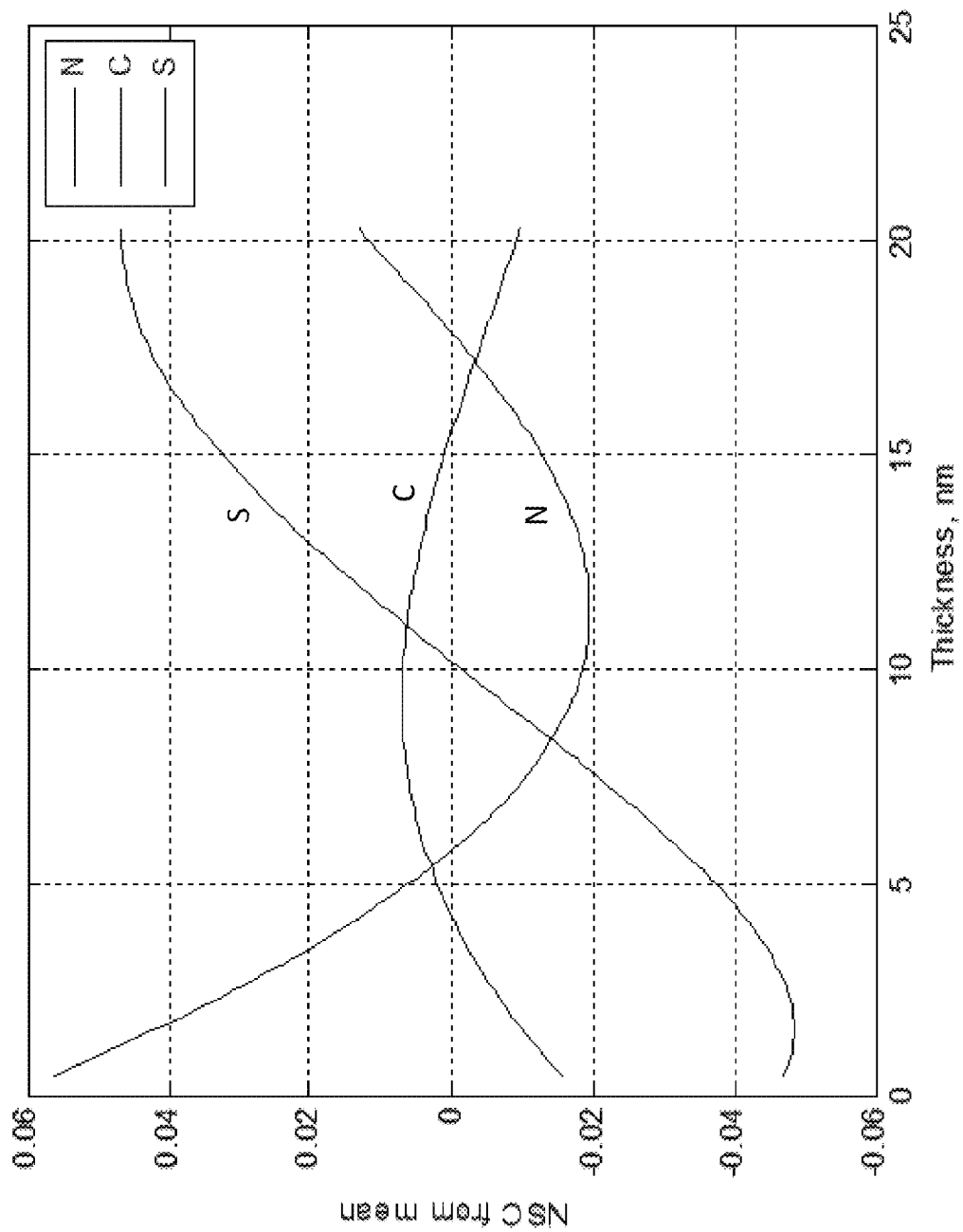
FIG. 9 is a graph comparing a measurable of reflection from a surface that can be deduced from the normalized results for the six signals of FIG. 3.

FIG. 9 is a graph comparing a measurable of reflection from a surface 108, wherein N, S, and C can be deduced from the normalized results for the six signals (D1-D6) of FIG. 3. N, S, and C are defined from the polarization characteristics of the surface 108 that are proportional to the different signal of each pair when the system is configured in a particular way, and may be linearly combined. In an instance, each of N, S, and C is proportional to one of the three pairs of normalized difference signals (e.g., D5 and D6, D1 and D2, D3 and D4). This is validated by noting that S has a similar shape to the V results illustrated in FIG. 8. The combination of N, S, and C provides more information than just, for example, S alone. Use of N, S, and C is more reliable against systematic error, such as irregularity of a wafer edge. For example, if the complex reflectance of the surface 108 is $R_s$, and $R_p$ for s- and p-polarization light, then $N=|R_p|-|R_s|$; $S=2Im(R_p^*conj(R_s))$; and $C=2Re(R_p^*conj(R_s))$.

Use of two or more normalized results can enable the system to measure thickness of a layer on the wafer at thicknesses in the 0 nm to 5 nm range. S alone cannot determine layer thickness in the 0 nm to 5 nm range due to ambiguity of one signal level corresponding to two different thickness. For example, S and N, S and C, or S, N, and C may provide adequate information to determine thickness of a layer on the wafer at thicknesses in the 0 nm to 5 nm range. N, S, and C vary with thickness. To determine the thickness, the quantities measured (combinations of N, S, and C) are determined mathematically in the desired thickness range. For example, the quantity S alone has same value at two different thickness in the range 0-3 nm range per FIG. 9 and N alone has same value at thickness 6 nm and 18 nm. Thus, the thickness cannot be determined with only one quantity alone.

The value of the layer on the wafer also can be determined based on the normalized result and a total intensity of the pair of the signals (e.g., Sp).

The extra information provided by S, N, and C can determine additional parameters.

For example, a combination of S, N, and C can be used to determine Ge concentration in a layer on a wafer in addition to its layer thickness. The extra information provided by S, N, and C can improve system accuracy and precision. For example, use of S, N, and C over-determine a thickness of a layer on a wafer. The values of, for example, the surface, thickness, concentration, and/or roughness are determined by fitting the measured signals (D1-D6, or their deduced quantities N, S, C) with a model of the system using, for example, nonlinear least square optimization algorithms.

While normalized results S, N, and C are disclosed, more or fewer normalized results may be used to determine a value of a layer on the wafer. For example, for a simpler structure of a layer or a smaller range of thicknesses to monitor, then only S or S and N may be used. For a more complex structure of a layer, then S, N, C, and an additional normalized result (Sp) may be used.

The system 100 may be calibrated prior to operation. The relationship between the signal(s) (e.g., D1-D6) and the sample optical property (e.g., N, S, C, or Sp) can depend on the configuration of the system 100. As, for example, the angle of a polarizing beam splitter changes, then the relationship between D1-D6 and N, S, and C also changes. Thus, the system 100 may be calibrated prior to operation. In an instance, a set of test wafers or a set of test structures on a calibration wafer with known characteristics is measured to provide a relationship between D1-D6 and N, S, and C. After this calibration process, sample optical characteristics (N, S, and C) can be calculated from the measured normalized results (D1-D6), so the relationship between D1-D6 and N, S, and C is determined.

A light source and detector wave-plate alignment procedure can be performed prior to operation of the system 100. This can set the angles of the optical axis to a designed value to keep the systems consistent.

While a $Si_{1-x}Ge_x$ epitaxial layer is disclosed, this system can be used with other layers or other types of wafers. For example, the system can determine thickness, critical dimension, and/or other values of a nitride layer, a silicon-on-insulator (SOI) wafer, a damaged layer on a wafer (e.g., an implanted layer), or other thin films formed using other types of deposition. In another example, the thickness of a silicon layer in a SOI wafer can be determined. In yet another example, the thickness of a silicon layer or implanted region (e.g., hydrogen-implanted region) in a wafer used in a wafer splitting or cleaving process can be determined. In yet another example, the thickness of an oxide layer that is grown on a wafer can be determined. In yet another example, the surface roughness or crystal slip-line of epitaxial layer of Si can be determined. In yet another example, the photoresist thickness can be determined pre and post EBR process.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. A system comprising:
   a stage configured to hold a wafer;
   a light source configured to direct a beam at a surface of the wafer on the stage;
   a sensor configured to receive the beam reflected off the surface and provide at least two polarization channels, each of the polarization channels providing a signal; and
   a controller in electronic communication with the sensor, wherein the controller is configured to:
   receive the signal from each of the polarization channels;
   normalize a difference between a pair of the signals to generate a normalized result; and
   determine a value of a layer on the wafer based on the normalized result and a total intensity of the pair of the signals, wherein the value is one of a thickness, a surface roughness, a material concentration, or a critical dimension.

2. The system of claim 1, wherein the sensor is a polarization sensitive detector.

3. The system of claim 1, wherein the sensor is configured to provide six of the polarization channels and wherein the sensor includes:
   a first beam splitter;
   a second beam splitter configured to receive light from the first beam splitter;
   a first polarizing beam splitter configured to receive light from the first beam splitter, wherein the first polarizing beam splitter is configured to generate two of the six polarization channels;
   a second polarizing beam splitter configured to receive light from the second beam splitter, wherein the second polarizing beam splitter is configured to generate two of the six polarization channels; and
   a third polarizing beam splitter configured to receive light from the second beam splitter, wherein the third polarizing beam splitter is configured to generate two of the six polarization channels.

4. The system of claim 3, wherein the first beam splitter is a 30/70 beam splitter.

5. The system of claim 3, wherein the second beam splitter is a 50/50 beam splitter.

6. The system of claim 3, wherein the second polarizing beam splitter is at 45° and the third polarizing beam splitter is at 0° with respect to an incident plane.

7. The system of claim 3, further comprising a quarter waveplate disposed between the first beam splitter and the first polarizing beam splitter.

8. The system of claim 3, wherein the controller is further configured to normalize pairs of the signals to generate three of the normalized results and determine the value based on the three normalized results.

9. The system of claim 1, wherein the controller is configured to normalize the difference between the pair of the signals using the formula $V=(Pq-Sq)/(Pq+Sq)$, wherein Pq and Sq are the pair of the signals, V is the normalized result, and $Sp=Pq+Sq$ is the total intensity.

10. The system of claim 1, wherein each of the polarization channels is generated by a polarizing beam splitter.

11. The system of claim 1, wherein the sensor is configured to provide four or fewer polarization channels of the beam reflected off the surface.

12. The system of claim 1, wherein the light source is configured to direct the beam at a plurality of wavelengths, and wherein the light source is a tunable laser or a wavelength multiplex of a plurality of lasers working at different wavelengths.

13. The system of claim 1, wherein the controller is configured to determine the value of the layer by fitting the pair of the signals or the normalized result with a nonlinear least square optimization algorithm.

14. A method comprising:
   directing a beam from a light source at a surface of a wafer;
   receiving the beam reflected off the surface with a sensor;
   splitting the beam in the sensor into a plurality of polarization channels using at least one polarizing beam splitter;
   generating a signal from each of the polarization channels;

normalizing a difference between a pair of the signals to generate a normalized result; and determining a value of a layer on the wafer based on the normalized result and a total intensity of the pair of the signals, wherein the value is one of a thickness, a surface roughness, a material concentration, or a critical dimension.

15. The method of claim 14, wherein the normalizing uses the formula $V=(Pq-Sq)/(Pq+Sq)$, wherein Pq and Sq are the pair of the signals, V is the normalized result, and $Sp=Pq+Sq$ is the total intensity.

16. The method of claim 14, wherein the splitting further comprises splitting the beam into six of the polarization channels using three of the polarizing beam splitters.

17. The method of claim 16, wherein the normalizing further comprises generating three of the normalized results.

18. The method of claim 14, further comprising using a model to analyze the measured signals for determining the value of a layer on the wafer.

19. The method of claim 14, wherein the beam is at a plurality of wavelengths, wherein the plurality of wavelengths is generated by a tunable laser or by a wavelength multiplex of a plurality of lasers working at different wavelengths.

20. The method of claim 14, wherein the determining comprises fitting the pair of the signals or the normalized result with a nonlinear least square optimization algorithm.

\* \* \* \* \*